(12) United States Patent
Neumann

(10) Patent No.: US 11,049,603 B1
(45) Date of Patent: Jun. 29, 2021

(54) SYSTEM AND METHOD FOR GENERATING A PROCREANT NOURISHMENT PROGRAM

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 0 days.

(21) Appl. No.: 17/136,199

(22) Filed: Dec. 29, 2020

(51) Int. Cl.
  *G16H 20/60* (2018.01)
  *G16H 50/70* (2018.01)
  *G16H 50/20* (2018.01)
  *G16H 40/67* (2018.01)

(52) U.S. Cl.
  CPC ............ *G16H 20/60* (2018.01); *G16H 40/67* (2018.01); *G16H 50/20* (2018.01); *G16H 50/70* (2018.01)

(58) Field of Classification Search
  None
  See application file for complete search history.

(56) References Cited

U.S. PATENT DOCUMENTS

| | | |
|---|---|---|
| 7,074,183 B2 | 7/2006 | Castellanos |
| 7,970,620 B2 | 6/2011 | Brown |
| 8,226,414 B2 | 7/2012 | Bodin |
| 8,560,336 B2 | 10/2013 | Schwarzberg |
| 8,684,922 B2 | 4/2014 | Tran |
| 10,373,522 B2 | 8/2019 | Byron |

(Continued)

FOREIGN PATENT DOCUMENTS

| | | |
|---|---|---|
| RU | 2691145 C2 | 6/2019 |
| WO | 2014015378 | 1/2014 |

(Continued)

OTHER PUBLICATIONS

Verma et al., Challenges in Personalized Nutrition and Health, Nov. 29, 2018, Front. Nutr. 5:117. doi: 10.3389/fnut.2018.00117 (Year: 2018).*

(Continued)

*Primary Examiner* — Devin C Hein
(74) *Attorney, Agent, or Firm* — Caldwell Intellectual Property Law, LLC

(57) ABSTRACT

A system and method for generating a procreant nourishment program comprises a computing device configured to obtain a procreant marker as a function of a procreant system, identify a procreant fascicle as a function of the procreant marker, wherein identifying comprises receiving an ilk parameter as a function of a biological database, retrieving a procreant functional goal, and identifying the procreant fascicle using a procreant machine-learning model, produce a procreant enumeration as a function of the procreant fascicle using an enumeration machine-learning model, determine a procreant appraisal as a function of the procreant enumeration, wherein determining comprises receiving a safe range as a function of a procreant recommendation, and determining the procreant appraisal as a function of the procreant enumeration and safe range, ascertain an edible as a function of the procreant appraisal, and generate a nourishment program as a function of the edible.

20 Claims, 8 Drawing Sheets

(56) References Cited

U.S. PATENT DOCUMENTS

| | | |
|---|---|---|
| 2002/0046060 A1 | 4/2002 | Hoskyns |
| 2006/0074279 A1 | 4/2006 | Brover |
| 2006/0199155 A1 | 9/2006 | Mosher |
| 2010/0042438 A1 | 2/2010 | Moore |
| 2010/0070455 A1 | 3/2010 | Halperin |
| 2010/0136508 A1 | 6/2010 | Zekhtser |
| 2013/0261183 A1 | 10/2013 | Bhagat |
| 2014/0255882 A1* | 9/2014 | Hadad .................. G16H 20/60 434/127 |
| 2014/0310019 A1* | 10/2014 | Blander ................ G16B 99/00 705/2 |
| 2015/0088541 A1* | 3/2015 | Yao ....................... G16H 20/00 705/2 |
| 2015/0161355 A1 | 6/2015 | Karra |
| 2015/0356885 A1 | 12/2015 | Chen |
| 2016/0225284 A1 | 8/2016 | Schoen |
| 2018/0308389 A1 | 10/2018 | Moser |
| 2019/0027232 A1* | 1/2019 | Beim .................... G16H 10/40 |
| 2019/0074080 A1 | 3/2019 | Appelbaum |
| 2019/0078142 A1* | 3/2019 | Apte ..................... G16H 50/30 |
| 2019/0221303 A1 | 7/2019 | Bennett |
| 2019/0251861 A1 | 8/2019 | Wolf |
| 2020/0138362 A1 | 5/2020 | Koumpan |

FOREIGN PATENT DOCUMENTS

| | | |
|---|---|---|
| WO | 2019054737 | 3/2019 |
| WO | 2019110412 | 6/2019 |
| WO | 2019229753 | 12/2019 |

OTHER PUBLICATIONS

Wang et al., Artificial Intelligence in Reproductive Medicine, Oct. 2019, Reproduction, 158(4):R139-R154. doi: 10.1530/REP-18-0523. (Year: 2019).*

Title: A Brief Tool to Assess Image-Based Dietary Records and Guide Nutrition Counselling Among Pregnant Women: An Evaluation; JMIR MHealth and UHealth vol. 4 Issue: 4 Article No. e123 Published: Oct.-Dec. 2016; by: Ashman.

Title: Biomarkers of Nutrition and Health: New Tools for New Approaches; Nutrients vol. 11 Issue: 5 Article No. 1092 Published: May 2019; by: Pico, Catalina.

Title: Role of Personalized Nutrition in Chronic-Degenerative Diseases; Nutrients vol. 11 Issue: 8 Article No. 1707 Published: Aug. 2019 DOI: 10.3390/nu11081707; by: Di Renzo, Laura.

* cited by examiner

SYSTEM AND METHOD FOR GENERATING A PROCREANT NOURISHMENT PROGRAM

FIELD OF THE INVENTION

The present invention generally relates to the field of artificial intelligence. In particular, the present invention is directed to a system and method for generating a procreant nourishment program

BACKGROUND

Current edible suggestion systems do not account for the procreant system of an individual. This leads to inefficiency of an edible suggestion system and a poor nutrition plan for the individual. This is further complicated by a lack of uniformity of nutritional plans, which results in dissatisfaction of individuals.

SUMMARY OF THE DISCLOSURE

In an aspect a system for generating a procreant nourishment program, the system comprising a computing device, the computing device configured to obtain at least a procreant marker as a function of a procreant system, identify a procreant fascicle as a function of the procreant marker, wherein identifying comprises receiving an ilk parameter as a function of a biological database, retrieving at least a procreant functional goal, and identifying the procreant fascicle as a function of the ilk parameter, procreant functional goal, and procreant marker using a procreant machine-learning model, produce a procreant enumeration as a function of the procreant fascicle using an enumeration machine-learning model, determine a procreant appraisal as a function of the procreant enumeration, wherein determining comprises receiving a safe range as a function of a procreant recommendation, and determining the procreant appraisal as a function of the procreant enumeration and safe range, ascertain an edible as a function of the procreant appraisal, and generate a nourishment program of a plurality of nourishment programs as a function of the edible.

In another aspect a method for generating a procreant nourishment program, the method comprising obtaining, by a computing device, at least a procreant marker as a function of a procreant system, identifying, by the computing device, a procreant fascicle as a function of the procreant marker, wherein identifying comprises receiving an ilk parameter as a function of a biological database, retrieving at least a procreant functional goal, and identifying the procreant fascicle as a function of the ilk parameter, procreant functional goal, and procreant marker using a procreant machine-learning model, producing, by the computing device, a procreant enumeration as a function of the procreant fascicle using an enumeration machine-learning model, determining, by the computing device, a procreant appraisal as a function of the procreant enumeration, wherein determining comprises receiving a safe range as a function of a procreant recommendation, and determining the procreant appraisal as a function of the procreant enumeration and safe range, ascertaining, by the computing device, an edible as a function of the procreant appraisal, and generating, by the computing device, a nourishment program of a plurality of nourishment programs as a function of the edible. These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for generating a procreant nourishment program. In an embodiment, the disclosure may obtain at least a procreant marker as a function of a procreant system. Aspects of the present disclosure can be used to identify a procreant fascicle as a function of the procreant marker. Aspects of the present disclosure can also be used to produce a procreant enumeration as a function of the procreant fascicle. This is so, at least in part, because the disclosure utilized an enumeration machine-learning process. Aspects of the present disclosure can be used to determine a procreant appraisal as a function of the procreant enumeration. Aspects of the present disclosure can also be used to ascertain an edible as a function of the procreant appraisal. Aspects of the present disclosure allow for generating a nourishment program as a function of the edible. Exemplary embodiments illustrating aspects of the present disclosure are described below in the context of several specific examples.

Figure 1:
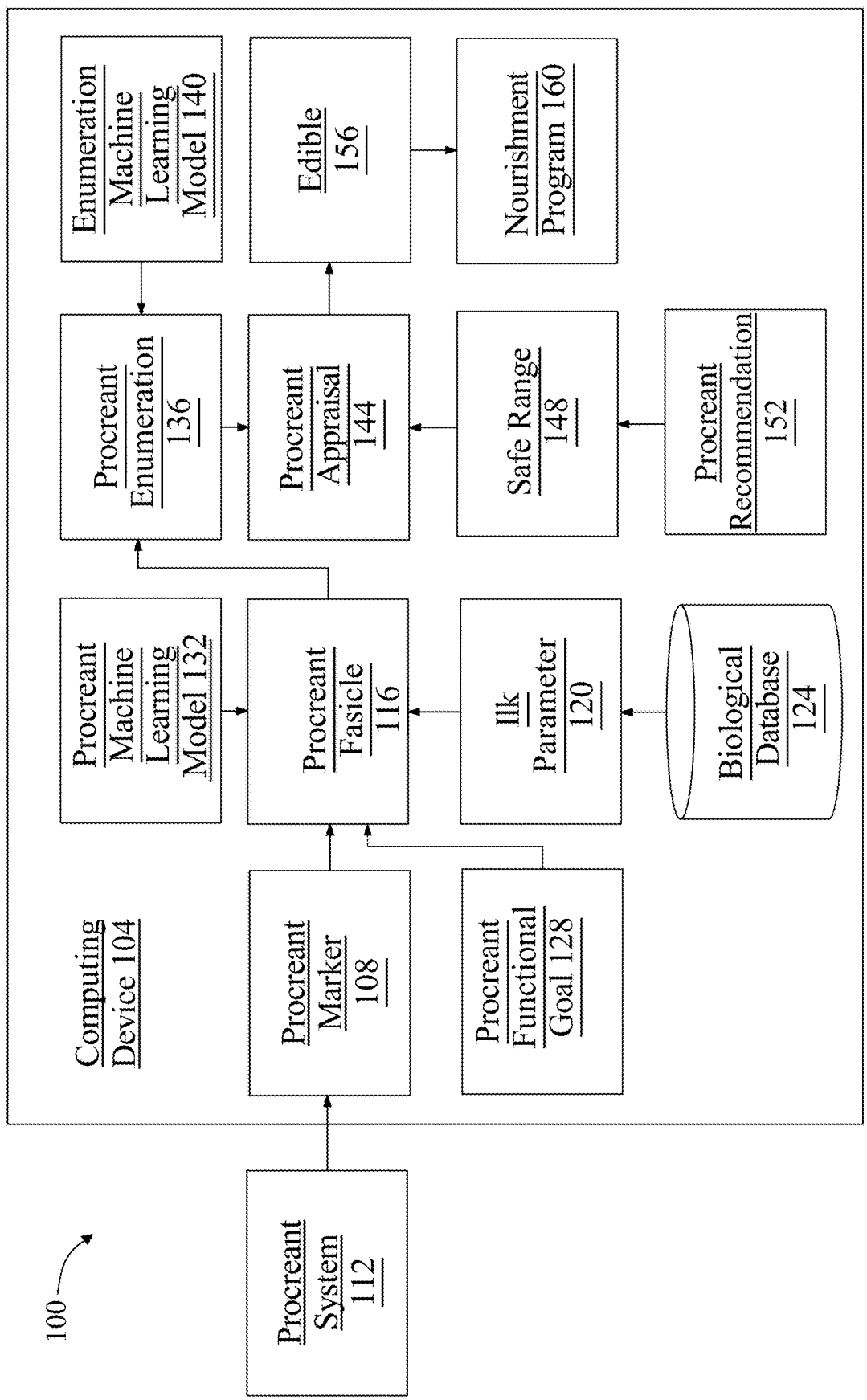
FIG. 1 is a block diagram illustrating an exemplary embodiment of a system for generating a procreant nourishment program.

Referring now to FIG. 1, an exemplary embodiment of a system 100 for generating a procreant nourishment program is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or as a function of a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 obtains at least a procreant marker 108. As used in this disclosure "procreant marker" is a marker that represents a health status of a user's procreant system. Procreant marker 108 may include a biological sample. As used in this disclosure "biological sample" is one or more biological specimens collected as a function of an individual. Biological sample may include, without limitation, blood, breath, sputum, urine, saliva, feces, semen, mucus, vaginal fluids, sebaceous oils, and other bodily fluids, as well as tissue. Procreant marker 108 may include tissue samples and/or cell samples from reproductive organs, wherein reproductive organs are described below. Procreant marker 108 may relate to one or more biomarkers. As used in this disclosure "biomarkers" are molecules, chemicals, components, and/or gases that at least identify the health status of a user's procreant system. As a non-limiting example biomarker may include, MLH1, MSH2, MSH6, PMS2, EPCAM, BRCA1, BRCA2, CHECK2, LH, FSH, progesterone, estrogen, androgen, prolactin, SHBG, testosterone, insulin, IGF1, IGF binding protein-1, PTEN genes, sterol regulatory binding protein-1, adiponectin, and the like thereof. As a non-limiting example procreant marker 108 may include a marker of androgen in a blood sample of an individual. As a further non-limiting example procreant marker 108 may include a hepatic cP450 in a bile sample of an individual. Procreant marker 108 is obtained as a function of a procreant system 112. As used in this disclosure "procreant system" is the reproductive system of an individual, wherein the reproductive system may include organs that contribute to the reproductive function of the human body. Organs of the reproductive system may include, without limitation, the ovary, fallopian tube, vagina, testes, uterus, penis, seminal vesicles, prostate, vas deferens, breasts, and the like thereof.

Still referring to FIG. 1, computing device 104 may obtain procreant marker 108 by receiving a procreant signal as a function of a sensor. As used in this disclosure "procreant signal" is datum that relates to and/or represents an element associated with the status of an individual's procreant system. As a non-limiting example a procreant signal may include an image of an ovary of an individual as a function of a magnetic resonance imaging medical device. As a further non-limiting example a procreant signal may include one or more lights, voltages, currents, sounds, chemicals, pressures, moistures, and the like thereof. As used in this disclosure "sensor" is a device that records, monitors, stores, measures, and/or transmits procreant signals. As a non-limiting example, a sensor may include an imaging sensor, such as optical cameras, infrared cameras, 3D cameras, multispectral cameras, hyperspectral cameras, polarized cameras, chemical sensors, motion sensors, ranging sensors, light radar component, such as lidar, detection or imaging using radio frequencies component, such as radar, terahertz or millimeter wave imagers, seismic sensors, magnetic sensors, weight/mass sensors, ionizing radiation sensors, and/or acoustical sensors. As a further non-limiting example, a sensor may include one or more medical examination devices. As used in this disclosure "medical examination devices" are devices that detect and/or monitor an individual's procreant system, such as semi-auto analyzers, photo colorimeters, cell photo colorimeters, hemoglobin meters, mass spectrometers, chromatographic instruments, and the like thereof.

Still referring to FIG. 1, computing device 104 identifies a procreant fascicle 116 as a function of procreant marker 108. As used in this disclosure "procreant fascicle" is a profile of a user's procreant status consisting of a group of procreant markers. Procreant fascicle may 116 may identify a profile as a function of sex, gender, reproductive organs, location of procreant marker origination, location of procreant marker termination, and the like thereof. As a non-limiting example procreant fascicle may identify a profile consisting of a group of procreant markers such as follicle stimulating hormone, estrogen, luteinizing hormone, progesterone, testosterone, dehydroepiandrosterone, cortisol, sex hormone binding globulin, triiodothyronine, thyroxine, thyroid stimulating hormone, and thyroid peroxidase antibodies relating to fertility of an individual. As a further non-limiting example, procreant fascicle 116 may identify a profile consisting of a group of procreant markers such as IL-1, IL-6, and CPK-MM relating to epididymitis of an individual. Computing device 104 identifies procreant fascicle 116 by receiving an ilk parameter 120. As used in this disclosure "ilk parameter" is a parameter associated with one or more biological classification elements. As a non-limiting example, ilk parameters may include sex, gender, culture, age, ethnicity, and the like thereof. Ilk parameter 120 is received as a function of a biological database 124, wherein a biological database identifies one or more ilk parameters associated with procreant system 112, as described below in detail, in reference to FIG. 4.

Still referring to FIG. 1, computing device 104 may classify a user datum to an ilk parameter. As used in this disclosure "user datum" is one or more biological classification elements associated with a user. For example, user datum may include a user's age, weight, height, reproductive goals, sex, gender, location, career, and the like thereof. Computing device 104 may classify user datum to at least identify one or more procreant commonalities among users. As used in this disclosure "procreant commonalities" are similarities that exist among two or more users that have similar ilk parameters. As a non-limiting example, procreant commonalities may identify that a midwestern suburban trans-male over the age of 50 may share similar reproductive goals of reducing fertility. As a further non-limiting example, procreant commonalities may identify that northeastern rural cis-females in the age range of 20-30 may share similar menstruation complications.

Still referring to FIG. 1, computing device 104 identifies procreant fascicle 116 by retrieving at least a procreant functional goal 128. As used in this disclosure "procreant functional goal" is a user desire, wish, want, and/or urge to alter and/or address a user concern. For example, and without limitation procreant functional goal 128 may include enhancing a user fertility. As a further non-limiting example procreant functional goal 128 may include reducing fertility and avoiding procreation. As a further non-limiting example procreant functional goal 128 may include a desire to enhance sexual performance and/or address erectile dysfunction concerns. As a further non-limiting example procreant functional goal 128 may include addressing irregular and/or painful menstruation cycles. Additionally and/or alternatively procreant functional goal may include a desire and/or wish to mitigate and/or diminish the effects of perimenopause and/or menopause. As a further non-limiting example procreant functional goal 128 may include a desire to adjust and/or alter hormone concentrations in an individual's body. Computing device 104 identifies procreant fascicle 116 as a function of ilk parameter 120, procreant functional goal 128, and procreant marker 108 using a procreant machine-learning model 132. As used in this disclosure "procreant machine-learning model" is a machine-learning model to produce a procreant fascicle output given ilk parameters, procreant functional goals, and procreant markers as inputs; this is in contrast to a non-machine learning software program where the commands to be executed are determined in advance by a user and written in a programming language. Procreant machine-learning model 132 may include one or more procreant machine-learning processes such as supervised, unsupervised, or reinforcement machine-learning processes that computing device 104 and/or a remote device may or may not use in the determination of procreant fascicle 116. As used in this disclosure "remote device" is an external device to computing device 104. A procreant machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train procreant machine-learning process as a function of a procreant training set. As used in this disclosure "procreant training set" is a training set that correlates an ilk parameter, procreant functional goal, and/or procreant marker to a procreant fascicle. For example, and without limitation, a procreant functional goal of hormone replacement, an ilk parameter of gender misassignment, and a procreant marker of an estrogen concentration of 124 pg/mL may relate to a procreant fascicle of trans-gender. As a further non-limiting example, a procreant functional goal of reduced scrotal pain, an ilk parameter of a male sex, and a procreant marker of IL-6 may relate to a procreant fascicle of inflammation of the epididymis. The procreant training set may be received as a function of user-entered valuations of ilk parameters, procreant functional goals, procreant markers, and/or procreant fascicles. Computing device 104 may receive procreant training by receiving correlations of ilk parameters, procreant functional goals, and or procreant markers that were previously received and/or determined during a previous iteration of determining procreant fascicles. The procreant training set may be received by one or more remote devices that at least correlate an ilk parameter, procreant functional goal, and/or procreant marker to a procreant fascicle, wherein a remote device is an external device to computing device 104, as described above. The procreant training set may be received by one or more user-entered correlations of an ilk parameter, procreant functional goal, and/or procreant marker to a procreant fascicle. Additionally or alternatively, a user may include an informed advisor, wherein an informed advisor may include, without limitation, urologists, reproductive endocrinologists, andrologists, reproductive immunologists, obstetrician-gynecologist, family physicians, family physicians, and the like thereof.

Still referring to FIG. 1, computing device 104 may receive procreant machine-learning model from a remote device that utilizes one or more procreant machine learning processes, wherein a remote device is described above in detail. For example, and without limitation, a remote device may include a computing device, external device, processor, and the like thereof. Remote device may perform the procreant machine-learning process using the procreant training set to generate procreant fascicle 128 and transmit the output to computing device 104. Remote device may transmit a signal, bit, datum, or parameter to computing device 104 that at least relates to procreant fascicle 128. Additionally or alternatively, the remote device may provide an updated machine-learning model. For example, and without limitation, an updated machine-learning model may be comprised of a firmware update, a software update, a procreant machine-learning process correction, and the like thereof. As a non-limiting example a software update may incorporate a new ilk parameter that relates to a modified procreant functional goal. Additionally or alternatively, the updated machine learning model may be transmitted to the remote device, wherein the remote device may replace the procreant machine-learning model with the updated machine-learning model and determine the procreant fascicle as a function of the ilk parameter using the updated machine-learning model. The updated machine-learning model may be transmitted by the remote device and received by computing device 104 as a software update, firmware update, or corrected procreant machine-learning model. For example, and without limitation a procreant machine-learning model may utilize a random forest machine-learning process, wherein the updated machine-learning model may incorporate a gradient boosting machine-learning process. Updated machine learning model may additionally or alternatively include any machine-learning model used as an updated machine learning model as described in U.S. Nonprovisional application Ser. No. 17/106,658, filed on Nov. 30, 2020, and entitled "A SYSTEM AND METHOD FOR GENERATING A DYNAMIC WEIGHTED COMBINATION," the entirety of which is incorporated herein by reference.

Still referring to FIG. 1, computing device 104 may identify procreant fascicle 116 by receiving a synergistic parameter as a function of procreant marker 108, wherein a synergistic parameter is a parameter that identifies one or more additional biomarkers that contribute to the same function in the human body described below in detail, in reference to FIG. 2. Computing device 104 may generate a procreant cluster as a function of synergistic parameter. As used in this disclosure "procreant cluster" is a cluster of is one or more procreant functions. As a non-limiting example procreant cluster may include one or more procreant functions associated with the production of egg cells. As a further non-limiting example procreant cluster may include one or more procreant functions associated with the production of spermatozoa. As a further non-limiting example procreant cluster may include one or more procreant functions associated with pregnancy and/or childbirth. As a further non-limiting example, procreant cluster may include one or more reproductive functions associated with puberty and/or maturation. Computing device 104 may identify procreant fascicle 116 as a function of procreant cluster.

Still referring to FIG. 1, procreant machine-learning model 132 may include a k-means clustering algorithm. A "k-means clustering algorithm" as used in this disclosure, includes cluster analysis that partitions n observations or unclassified cluster data entries into k clusters in which each observation or unclassified cluster data entry belongs to the cluster with the nearest mean, using, for instance behavioral training set as described above. "Cluster analysis" as used in this disclosure, includes grouping a set of observations or data entries in way that observations or data entries in the same group or cluster are more similar to each other than to those in other groups or clusters. Cluster analysis may be performed by various cluster models that include connectivity models such as hierarchical clustering, centroid models such as k-means, distribution models such as multivariate normal distribution, density models such as density-based spatial clustering of applications with nose (DBSCAN) and ordering points to identify the clustering structure (OPTICS), subspace models such as biclustering, group models, graph-based models such as a clique, signed graph models, neural models, and the like. Cluster analysis may include hard clustering whereby each observation or unclassified cluster data entry belongs to a cluster or not. Cluster analysis may include soft clustering or fuzzy clustering whereby each observation or unclassified cluster data entry belongs to each cluster to a certain degree such as for example a likelihood of belonging to a cluster; for instance, and without limitation, a fuzzy clustering algorithm may be used to identify clustering of gene combinations with multiple disease states, and vice versa. Cluster analysis may include strict partitioning clustering whereby each observation or unclassified cluster data entry belongs to exactly one cluster. Cluster analysis may include strict partitioning clustering with outliers whereby observations or unclassified cluster data entries may belong to no cluster and may be considered outliers. Cluster analysis may include overlapping clustering whereby observations or unclassified cluster data entries may belong to more than one cluster. Cluster analysis may include hierarchical clustering whereby observations or unclassified cluster data entries that belong to a child cluster also belong to a parent cluster.

With continued reference to FIG. 1, computing device may generate a k-means clustering algorithm receiving unclassified physiological state data and outputs a definite number of classified data entry clusters wherein the data entry clusters each contain cluster data entries. K-means algorithm may select a specific number of groups or clusters to output, identified by a variable "k." Generating a k-means clustering algorithm includes assigning inputs containing unclassified data to a "k-group" or "k-cluster" based on feature similarity. Centroids of k-groups or k-clusters may be utilized to generate classified data entry cluster. K-means clustering algorithm may select and/or be provided "k" variable by calculating k-means clustering algorithm for a range of k values and comparing results. K-means clustering algorithm may compare results across different values of k as the mean distance between cluster data entries and cluster centroid. K-means clustering algorithm may calculate mean distance to a centroid as a function of k value, and the location of where the rate of decrease starts to sharply shift, this may be utilized to select a k value. Centroids of k-groups or k-cluster include a collection of feature values which are utilized to classify data entry clusters containing cluster data entries. K-means clustering algorithm may act to identify clusters of closely related physiological data, which may be provided with user cohort labels; this may, for instance, generate an initial set of user cohort labels from an initial set of user physiological data of a large number of users, and may also, upon subsequent iterations, identify new clusters to be provided new user cohort labels, to which additional user physiological data may be classified, or to which previously used user physiological data may be reclassified.

With continued reference to FIG. 1, generating a k-means clustering algorithm may include generating initial estimates for k centroids which may be randomly generated or randomly selected from unclassified data input. K centroids may be utilized to define one or more clusters. K-means clustering algorithm may assign unclassified data to one or more k-centroids based on the squared Euclidean distance by first performing a data assigned step of unclassified data. K-means clustering algorithm may assign unclassified data to its nearest centroid based on the collection of centroids $c_i$ of centroids in set C. Unclassified data may be assigned to a cluster based on $argmin_{ci \ni c}$ dist(ci, x)$^2$, where argmin includes argument of the minimum, ci includes a collection of centroids in a set C, and dist includes standard Euclidean distance. K-means clustering module may then recompute centroids by taking mean of all cluster data entries assigned to a centroid's cluster. This may be calculated based on ci=1/|Si|Σxi $\ni$ Si$^{xi}$ K-means clustering algorithm may continue to repeat these calculations until a stopping criterion has been satisfied such as when cluster data entries do not change clusters, the sum of the distances have been minimized, and/or some maximum number of iterations has been reached.

Still referring to FIG. 1, k-means clustering algorithm may be configured to calculate a degree of similarity index value. A "degree of similarity index value" as used in this disclosure, includes a distance measurement indicating a measurement between each data entry cluster generated by k-means clustering algorithm and a selected physiological data set. Degree of similarity index value may indicate how close a particular combination of genes, negative behaviors and/or negative behavioral propensities is to being classified by k-means algorithm to a particular cluster. K-means clustering algorithm may evaluate the distances of the combination of genes, negative behaviors and/or negative behavioral propensities to the k-number of clusters output by k-means clustering algorithm. Short distances between a set of physiological data and a cluster may indicate a higher degree of similarity between the set of physiological data and a particular cluster. Longer distances between a set of physiological behavior and a cluster may indicate a lower degree of similarity between a physiological data set and a particular cluster.

With continued reference to FIG. 1, k-means clustering algorithm selects a classified data entry cluster as a function of the degree of similarity index value. In an embodiment, k-means clustering algorithm may select a classified data entry cluster with the smallest degree of similarity index value indicating a high degree of similarity between a physiological data set and the data entry cluster. Alternatively or additionally k-means clustering algorithm may select a plurality of clusters having low degree of similarity index values to physiological data sets, indicative of greater degrees of similarity. Degree of similarity index values may be compared to a threshold number indicating a minimal degree of relatedness suitable for inclusion of a set of physiological data in a cluster, where degree of similarity indices a-n falling under the threshold number may be included as indicative of high degrees of relatedness. The above-described illustration of feature learning using k-means clustering is included for illustrative purposes only, and should not be construed as limiting potential implementation of feature learning algorithms; persons skilled in the art, upon reviewing the entirety of this disclosure, will be aware of various additional or alternative feature learning and/or clustering approaches that may be used consistently with this disclosure, including without limitation clustering algorithms based on particle swarm optimization (PSO), ant colony optimization (ACO), neural networks, deep learning networks, and the like.

Still referring to FIG. 1, computing device 104 produces a procreant enumeration 136. As used in this this disclosure "procreant enumeration" is a measurable value associated with a procreant impact. As a non-limiting example procreant enumeration 136 may be a value of 13 for a procreant impact of sterility. As a further non-limiting example procreant enumeration 136 may be a value of 25 for a procreant impact of severe abdominal cramps. Computing device 104 determines procreant enumeration 136 using an enumeration machine-learning model 140. As used in this disclosure "enumeration machine-learning model" is a machine-learning model to produce a procreant enumeration output given a procreant fascicle and procreant impacts as inputs; this is in contrast to a non-machine learning software program where the commands to be executed are determined in advance by a user and written in a programming language. Enumeration machine-learning model may include one or more enumeration machine-learning processes such as supervised, unsupervised, or reinforcement machine-learning processes that computing device 104 and/or a remote device may or may not use in the determination of procreant appraisal. An enumeration machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train enumeration machine-learning process as a function of an enumeration training set. As used in this disclosure "enumeration training set" is a training set that correlates at least a procreant fascicle to a procreant impact. As a non-limiting example a procreant fascicle of reduced fertility may relate to a procreant impact of 36. The enumeration training set may be received as a function of user-entered valuations of procreant fascicle, procreant impact, and/or procreant enumeration. Computing device 104 may receive enumeration training by receiving correlations of a procreant fascicles and/or procreant impacts that were previously received and/or determined during a previous iteration of determining procreant enumeration. The enumeration training set may be received by one or more remote devices that at least correlate procreant fascicles and/or procreant impacts to procreant enumeration, wherein a remote device is an external device to computing device 104, as described above. The enumeration training set may be received by one or more user-entered correlations of a procreant fascicle and/or procreant impact to procreant enumeration. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, computing device 104 may receive enumeration machine-learning model 152 from a remote device that utilizes one or more enumeration machine learning processes, wherein a remote device is described above in detail. For example, and without limitation, a remote device may include a computing device, external device, processor, and the like thereof. Remote device may perform the enumeration machine-learning process using the enumeration training set to generate procreant enumeration and transmit the output to computing device 104. Remote device may transmit a signal, bit, datum, or parameter to computing device 104 that at least relates to procreant enumerations. Additionally or alternatively, the remote device may provide an updated machine-learning model. For example, and without limitation, an updated machine-learning model may be comprised of a firmware update, a software update, an enumeration machine-learning process correction, and the like thereof. As a non-limiting example a software update may incorporate a new procreant fascicle that relates to a modified procreant impact. Additionally or alternatively, the updated machine learning model may be transmitted to the remote device, wherein the remote device may replace the enumeration machine-learning model with the updated machine-learning model and determine the procreant enumeration as a function of the procreant impact using the updated machine-learning model. The updated machine-learning model may be transmitted by the remote device and received by computing device 104 as a software update, firmware update, or corrected enumeration machine-learning model. For example, and without limitation procreant machine-learning model may utilize a logistic classification machine-learning process, wherein the updated machine-learning model may incorporate linear discriminant analysis machine-learning process.

Still referring to FIG. 1, computing device 104 may produce procreant enumeration 136 by identifying a procreant disorder. As used in this disclosure "procreant disorder" is an ailment and/or collection of ailments that impact an individual's reproductive system. As a non-limiting example, procreant disorder may include prostate cancer, testicular cancer, prostatitis, erectile dysfunction, male infertility, testosterone deficiency, epididymitis varicocele, Lynch syndrome, endometriosis, uterine fibroids, dysmenorrhea, cervical cancer, familial breast cancer, pelvic inflammatory disease, and the like thereof. Procreant disorder may be identified as a function of one or more disorder machine-learning models. As used in this disclosure "disorder machine-learning model" is a machine-learning model to produce a procreant disorder output given procreant fascicles as inputs; this is in contrast to a non-machine learning software program where the commands to be executed are determined in advance by a user and written in a programming language. Disorder machine-learning model may include one or more disorder machine-learning processes such as supervised, unsupervised, or reinforcement machine-learning processes that computing device 104 and/or a remote device may or may not use in the determination of procreant disorder. A disorder machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train disorder machine-learning process as a function of a disorder training set. As used in this disclosure "disorder training set" is a training set that correlates at least a procreant system effect and procreant fascicle 116 to a procreant disorder. As used in this disclosure "procreant system effect" is an impact and/or effect on the procreant system of an individual. As a non-limiting example a procreant fascicle of reduced testosterone may be established for a procreant system effect of infertility, wherein a procreant disorder of infertility may be determined. The disorder training set may be received as a function of user-entered valuations of procreant fascicle 116, procreant system effects, and/or procreant disorders. Computing device 104 may receive disorder training by receiving correlations of procreant fascicle 116 and/or procreant system effects that were previously received and/or determined during a previous iteration of determining procreant disorders. The disorder training set may be received by one or more remote devices that at least correlate procreant fascicle 116 and/or procreant system effect to a procreant disorder, wherein a remote device is an external device to computing device 104, as described above. The disorder training set may be received by one or more user-entered correlations of a procreant fascicle and procreant system effect to a procreant disorder. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, computing device 104 may receive disorder machine-learning model from a remote device that utilizes one or more disorder machine learning processes, wherein a remote device is described above in detail. For example, and without limitation, a remote device may include a computing device, external device, processor, and the like thereof. Remote device may perform the disorder machine-learning process using the disorder training set to generate procreant disorder and transmit the output to computing device 104. Remote device may transmit a signal, bit, datum, or parameter to computing device 104 that at least relates to procreant disorders. Additionally or alternatively, the remote device may provide an updated machine-learning model. For example, and without limitation, an updated machine-learning model may be comprised of a firmware update, a software update, a disorder machine-learning process correction, and the like thereof. As a non-limiting example a software update may incorporate a new procreant fascicle that relates to a modified procreant system effect. Additionally or alternatively, the updated machine learning model may be transmitted to the remote device, wherein the remote device may replace the disorder machine-learning model with the updated machine-learning model and determine the procreant disorder as a function of the procreant fascicle using the updated machine-learning model. The updated machine-learning model may be transmitted by the remote device and received by computing device 104 as a software update, firmware update, or corrected dysfunction machine-learning model. For example, and without limitation procreant machine-learning model may utilize a neural net machine-learning process, wherein the updated machine-learning model may incorporate hierarchical clustering machine-learning process.

Still referring to FIG. 1, computing device 104 determines a procreant appraisal 144 as a function of procreant enumeration 136. As used in this disclosure "procreant appraisal" is a quantitative value associated with the severity of procreant enumeration. Computing device 104 determines procreant appraisal 144 by receiving a safe range 148. As used in this disclosure "safe range" is a reference range and/or reference interval for a normal physiologic measurement of a procreant marker. As a non-limiting example procreant fascicle 116 may identify a serum endocannabinoid concentration of 5.2 nM, wherein a safe range of serum endocannabinoid concentrations for fertility may be 10-500 nM. As a further non-limiting example, procreant fascicle 116 may determine a HER2/neu concentration of 65.38 ng/mL, wherein a wherein a safe range of HER2/neu may be 12.2-25.6 ng/mL. Safe range 148 is received as a function of a procreant recommendation 152. As used in this disclosure "procreant recommendation" is a medical guideline for the measurement of procreant system health. As a non-limiting example procreant recommendation 152 may be identified by one or more organizations that relate to, represent, and/or study procreant functions in humans, such as The American Society for Reproductive Medicine, Reproductive Medicine Associates, Society for Assisted Reproductive Technology, and the like thereof. As a further non-limiting example, procreant recommendation 152 may determine safe range 148 as a function of one or more medical research journals, such as Reproductive Sciences, Reproductive Biomedicine Online, Reproductions, Biology of Reproduction, The Lancet, New England Journal of Medicine, Science, Journal of the American Medical Association, and the like thereof.

Still referring to FIG. 1, Computing device 104 may determine procreant appraisal 136 as a function of generating a degree of variance. As used in this disclosure "degree of variance" is a quantitative value comprising the magnitude of divergence of procreant enumeration 148 and safe range 140. As a non-limiting example, a degree of variance may be 12 for a procreant enumeration of 0.22 µg/mL of progesterone, wherein the safe range 0.08-0.12 µg/mL of progesterone. Degree of variance may include a transgression parameter. As used in this disclosure "transgression parameter" is a parameter that identifies one or more degrees of variance that exceed a variance limit. As a non-limiting example, transgression parameter may determine that a degree of variance should not exceed 10 for the biomarker inhibin. As a further non-limiting, transgression parameter may determine that a degree of variance should not exceed 2 for a vascular endothelial growth factor.

Still referring to FIG. 1, computing device 104 ascertains at least an edible 156 as a function of procreant appraisal 144. As used in this disclosure an "edible" is a source of nourishment that may be consumed by a user such that the user may absorb the nutrients from the source. For example and without limitation, an edible may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. Computing device 104 may ascertain edible 156 as a function of obtaining a nourishment composition. As used in this disclosure "nourishment composition" is a list and/or compilation of all of the nutrients contained in an edible. As a non-limiting example nourishment composition may include one or more quantities and/or amounts of total fat, including saturated fat and/or trans-fat, cholesterol, sodium, total carbohydrates, including dietary fiber and/or total sugars, protein, vitamin A, vitamin C, thiamin, riboflavin, niacin, pantothenic acid, vitamin b6, folate, biotin, vitamin B12, vitamin D, vitamin E, vitamin K, calcium, iron, phosphorous, iodine, magnesium, zinc, selenium, copper, manganese, chromium, molybdenum, chloride, and the like thereof. Nourishment composition may be obtained as a function of an edible directory, wherein an edible directory is a database of edibles that may be identified as a function of one or more procreant appraisals, as described in detail below, in reference to FIG. 3.

Still referring to FIG. 1, computing device 104 may ascertain edible 156 as a function of nourishment composition, procreant appraisal 144, and an edible machine-learning model. As used in this disclosure "edible machine-learning model" is a machine-learning model to produce an edible output given nourishment compositions and procreant appraisals as inputs; this is in contrast to a non-machine learning software program where the commands to be executed are determined in advance by a user and written in a programming language. Edible machine-learning model may include one or more edible machine-learning processes such as supervised, unsupervised, or reinforcement machine-learning processes that computing device 104 and/or a remote device may or may not use in ascertaining edible 156. An edible machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train edible machine-learning process as a function of an edible training set. As used in this disclosure a "edible training set" is a training set that correlates at least nourishment composition and procreant appraisal to an edible. For example, and without limitation, nourishment composition of 500 ng/mL of estrogen and a procreant appraisal of infertility may relate to an edible of edamame. The edible training set may be received as a function of user-entered valuations of nourishment compositions, procreant appraisals, and/or edibles. Computing device 104 may receive edible training by receiving correlations of nourishment compositions and/or procreant appraisals that were previously received and/or determined during a previous iteration of ascertaining edibles. The edible training set may be received by one or more remote devices that at least correlate a nourishment composition and procreant appraisal to an edible, wherein a remote device is an external device to computing device 104, as described above. The edible training set may be received by one or more user-entered correlations of a nourishment composition and procreant appraisal to an edible. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, edible machine-learning model may ascertain edible 156 as a function of one or more classifiers. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a processes whereby a computing device 104 derives a classifier from training data. Classification may be performed using, without limitation, linear classifiers such as without limitation logistic regression and/or naïve Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn as a function of a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)÷P(B), where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least one value. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1, computing device 104 may receive edible machine-learning model from a remote device that utilizes one or more edible machine learning processes, wherein a remote device is described above in detail. For example, and without limitation, a remote device may include a computing device, external device, processor, and the like thereof. Remote device may perform the edible machine-learning process using the edible training set to ascertain edible 156 and transmit the output to computing device 104. Remote device may transmit a signal, bit, datum, or parameter to computing device 104 that at least relates to edible 156. Additionally or alternatively, the remote device may provide an updated machine-learning model. For example, and without limitation, an updated machine-learning model may be comprised of a firmware update, a software update, an edible machine-learning process correction, and the like thereof. As a non-limiting example a software update may incorporate a new nourishment composition that relates to a modified procreant appraisal. Additionally or alternatively, the updated machine learning model may be transmitted to the remote device, wherein the remote device may replace the edible machine-learning model with the updated machine-learning model and ascertain the edible as a function of the procreant appraisal using the updated machine-learning model. The updated machine-learning model may be transmitted by the remote device and received by computing device 104 as a software update, firmware update, or corrected edible machine-learning model. For example, and without limitation an edible machine-learning model may utilize a Naïve Bayes machine-learning process, wherein the updated machine-learning model may incorporate a logistic regression machine-learning process. Updated machine learning model may additionally or alternatively include any machine-learning model used as an updated machine learning model as described in U.S. Nonprovisional application Ser. No. 17/106,658.

Still referring to FIG. 1, computing device 104 may ascertain edible 156 as a function of a likelihood parameter. As used in this disclosure "likelihood parameter" is a parameter that identifies the probability of a user to consume an edible. As a non-limiting example likelihood parameter may identify a high probability that a user will consume an edible of chicken. As a further non-limiting example likelihood parameter may identify a low probability that a user will consume an edible of Brussel sprouts. Likelihood parameter may be determined as a function of a user taste profile. As used in this disclosure "user taste profile" is a profile of a user that identifies one or more desires, preferences, wishes, and/or wants that a user has. As a non-limiting example a user taste profile may include a user's preference for beef flavor and/or soft textured edibles. Likelihood parameter may be determined as a function of an edible profile. As used in this disclosure "edible profile" is taste of an edible is the sensation of flavor perceived in the mouth and throat on contact with the edible. Edible profile may include one or more flavor variables. As used in this disclosure "flavor variable" is a variable associated with the distinctive taste of an edible, wherein a distinctive may include, without limitation sweet, bitter, sour, salty, umami, cool, and/or hot. Edible profile may be determined as a function of receiving flavor variable as a function of a flavor directory. As used in this disclosure "flavor directory" is a database of flavors for an edible. As a non-limiting example flavor directory may include a list and/or collection of edibles that all contain umami flavor variables. As a further non-limiting example flavor directory may include a list and/or collection of edibles that all contain sour flavor variables. Likelihood parameter may alternatively or additionally include any user taste profile and/or edible profile used as a likelihood parameter as described in U.S. Nonprovisional application Ser. No. 17/032,080, filed on Sep. 25, 2020, and entitled "METHODS, SYSTEMS, AND DEVICES FOR GENERATING A REFRESHMENT INSTRUCTION SET BASED ON INDIVIDUAL PREFERENCES," the entirety of which is incorporated herein by reference.

Still referring to FIG. 1, computing device 104 generates a nourishment program 160 of a plurality of nourishment programs as a function of edible 156. As used in this disclosure "nourishment program" is a program consisting of one or more edibles that are to be consumed over a given time period, wherein a time period is a temporal measurement such as seconds, minutes, hours, days, weeks, months, years, and the like thereof. As a non-limiting example nourishment program 160 may consist of recommending ice cream for 2 days. As a further non-limiting example nourishment program 160 may recommend tofu for a first day, *quinoa* for a second day, and broccoli for a third day. Nourishment program 160 may include one or more diet programs such as paleo, keto, vegan, vegetarian, and the like thereof. Computing device 104 generates nourishment program as a function of a procreant outcome. As used in this disclosure "procreant outcome" is an outcome that an edible may generate according to a predicted and/or purposeful plan. As a non-limiting example, procreant outcome may include a treatment outcome. As used in this disclosure "treatment outcome" is an intended outcome that is designed to at least reverse and/or eliminate procreant appraisal 144 associated with procreant fascicle 116 and/or procreant disorder. As a non-limiting example, a treatment outcome may include reversing the effects of the procreant disorder of endometriosis. As a further non-limiting example, a treatment outcome includes reversing the procreant disorder of dysmenorrhea. Procreant outcome may include a prevention outcome. As used in this disclosure "prevention outcome" is an intended outcome that is designed to at least prevent and/or avert procreant appraisal 144 associated with procreant fascicle 116 and/or procreant disorder. As a non-limiting example, a prevention outcome may include preventing the development of the procreant disorder of infertility.

Still referring to FIG. 1, computing device 104 may generate nourishment program 160 function of edible 156 and procreant outcome using a nourishment machine-learning model. As used in this disclosure "nourishment machine-learning model" is a machine-learning model to produce a nourishment program output given edibles and/or procreant outcomes as inputs; this is in contrast to a non-machine learning software program where the commands to be executed are determined in advance by a user and written in a programming language. Nourishment machine-learning model may include one or more nourishment machine-learning processes such as supervised, unsupervised, or reinforcement machine-learning processes that computing device 104 and/or a remote device may or may not use in the determination of nourishment program 160. Nourishment machine-learning process may include, without limitation machine learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, computing device 104 may train nourishment machine-learning process as a function of a nourishment training set. As used in this disclosure a "nourishment training set" is a training set that correlates a procreant outcome to an edible. The nourishment training set may be received as a function of user-entered edibles, procreant outcomes, and/or nourishment programs. Computing device 104 may receive nourishment training by receiving correlations of procreant outcomes and/or edibles that were previously received and/or determined during a previous iteration of determining nourishment programs. The nourishment training set may be received by one or more remote devices that at least correlate a procreant outcome and/or edible to a nourishment program, wherein a remote device is an external device to computing device 104, as described above. The nourishment training set may be received by one or more user-entered correlations of a procreant outcome and edible to a nourishment program. Additionally or alternatively, a user may include an informed advisor, wherein an informed advisor may include, without limitation, urologists, reproductive endocrinologists, andrologists, reproductive immunologists, obstetrician-gynecologist, family physicians, and the like thereof.

Still referring to FIG. 1, computing device 104 may receive nourishment machine-learning model 156 from a remote device that utilizes one or more nourishment machine learning processes, wherein a remote device is described above in detail. For example, and without limitation, a remote device may include a computing device, external device, processor, and the like thereof. Remote device may perform the nourishment machine-learning process using the nourishment training set to generate nourishment program 160 and transmit the output to computing device 104. Remote device may transmit a signal, bit, datum, or parameter to computing device 104 that at least relates to nourishment program 160. Additionally or alternatively, the remote device may provide an updated machine-learning model. For example, and without limitation, an updated machine-learning model may be comprised of a firmware update, a software update, a nourishment machine-learning process correction, and the like thereof. As a non-limiting example a software update may incorporate a new procreant outcome that relates to a modified edible. Additionally or alternatively, the updated machine learning model may be transmitted to the remote device, wherein the remote device may replace the nourishment machine-learning model with the updated machine-learning model and determine the nourishment program as a function of the procreant outcome using the updated machine-learning model. The updated machine-learning model may be transmitted by the remote device and received by computing device 104 as a software update, firmware update, or corrected nourishment machine-learning model. For example, and without limitation nourishment machine-learning model may utilize a decision tree machine-learning process, wherein the updated machine-learning model may incorporate linear regression machine-learning processes.

Figure 2:
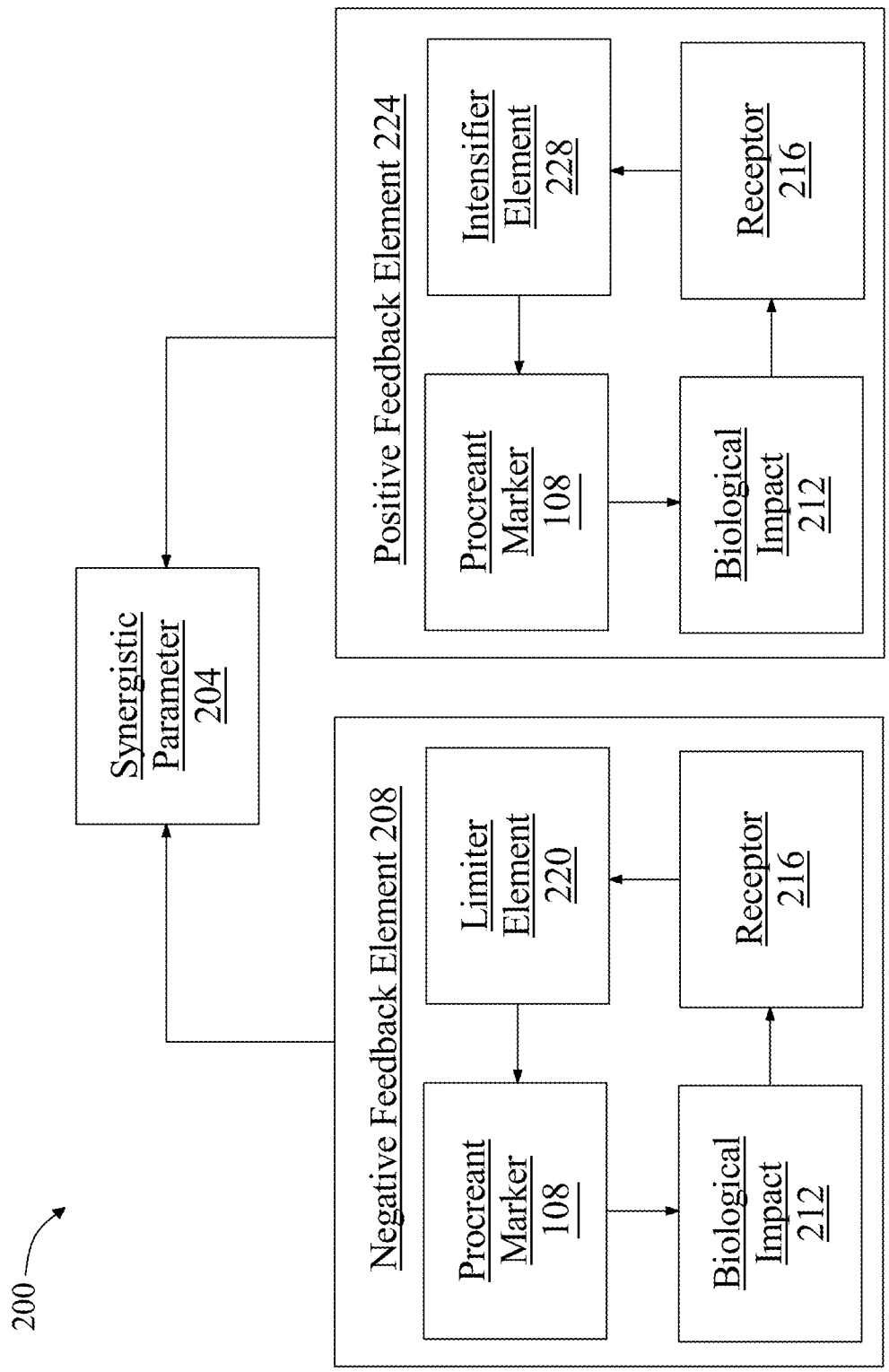
FIG. 2 is a representative diagram of an exemplary embodiment of synergistic parameters according to an embodiment of the invention.

Now referring to FIG. 2, an exemplary embodiment 200 of a synergistic parameter 204 according to an embodiment of the invention is illustrated. As used in this disclosure "synergistic parameter" is a parameter that identifies one or more additional biomarkers that contribute to the same function in the human body. As a non-limiting example a synergistic parameter may be identified for the biomarkers such as 25-hydroxyvitamin D, vitamin D binding protein, and parathyroid hormone, wherein each of the biomarkers relate to the absorption and regulation of vitamin D. Synergistic parameter 204 may include a negative feedback element 208. As used in this disclosure "negative feedback element" is an element that reduces the output of the input. As a non-limiting example negative feedback element may relate to an input of the biomarker glucose, wherein the output is insulin, such that the glucose is reduced. Negative feedback element 208 may receive procreant marker 108 and identify a biological impact 212. As used in this disclosure "biological impact" is an effect that a procreant marker has on the procreant system of an individual. As a non-limiting example, biological impact 212 may include an impact associated with an increase of testosterone in the procreant system. Biological impact 212 may be determined as a function of a receptor 216. As used in this disclosure "receptor" is a special structure found in procreant system that at least binds to specialized molecules using a lock and key mechanism. As a non-limiting examples receptor 216 may include estrogen receptors, CB2 receptors, testosterone receptors, endocannabinoid receptors, and the like thereof. Negative feedback element 208 may determine a limiter element 220 as a function of receptor 216. As used in this disclosure "limiter element" is an element that reduces and/or minimizes procreant marker 108. As a non-limiting example a limiter element may include gonadotropin-releasing hormone, wherein gonadotropin-releasing hormone may inhibit the production of estrogen. Synergistic parameter 204 may include a positive feedback element 224. As used in this disclosure "positive feedback element" is an element that enhances the output of the input. As a non-limiting example positive feedback element may include childbirth, wherein pressure on the cervix stimulates the release of oxytocin, which stimulates further contractions and additional pressure on the cervix. Positive feedback element 224 may include biological input 212 as described in detail above. Positive feedback element 224 may include receptor 216 as described above in detail. Positive feedback element 224 may determine an intensifier element 228 as a function of receptor 216. As used in this disclosure "intensifier element" is an element that enhances and/or maximizes procreant marker 108. As a non-limiting example intensifier element 228 may include TF:VII activation by FXa, wherein FXa enhances the activation and/or production of TF:VII to produce more blood clotting.

Figure 3:
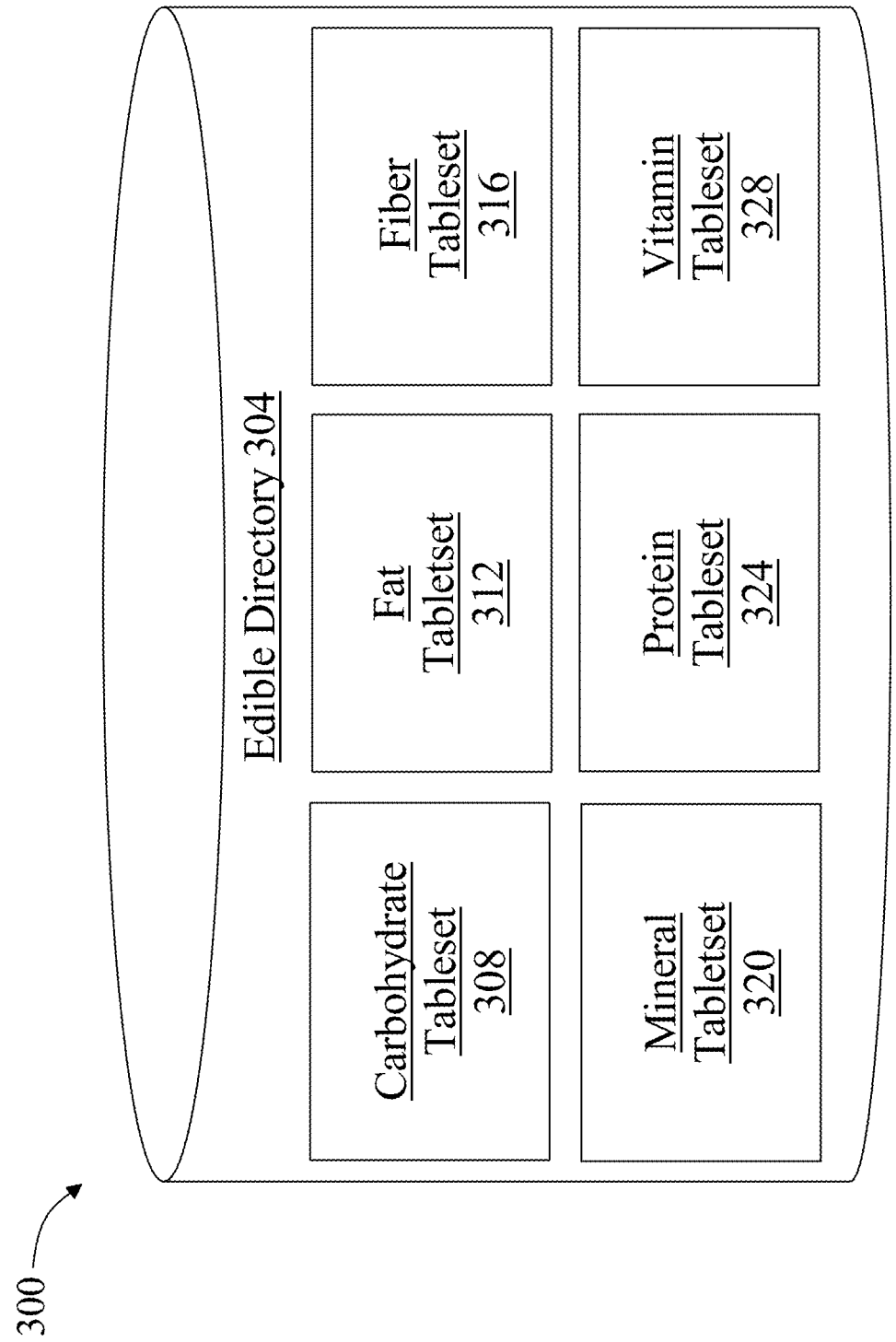
FIG. 3 is a block diagram of an exemplary embodiment of an edible directory according to an embodiment of the invention.

Now referring to FIG. 3, an exemplary embodiment 300 of an edible directory 304 according to an embodiment of the invention is illustrated. Edible directory 304 may be implemented, without limitation, as a relational databank, a key-value retrieval databank such as a NOSQL databank, or any other format or structure for use as a databank that a person skilled in the art would recognize as suitable upon review of the entirety of this disclosure. Edible directory 304 may alternatively or additionally be implemented using a distributed data storage protocol and/or data structure, such as a distributed hash table or the like. Edible directory 304 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Edible directory 304 may include a carbohydrate tableset 308. Carbohydrate tableset 308 may relate to a nourishment composition of an edible with respect to the quantity and/or type of carbohydrates in the edible. As a non-limiting example, carbohydrate tableset 308 may include monosaccharides, disaccharides, oligosaccharides, polysaccharides, and the like thereof. Edible directory 304 may include a fat tableset 312. Fat tableset 312 may relate to a nourishment composition of an edible with respect to the quantity and/or type of esterified fatty acids in the edible. Fat tableset 312 may include, without limitation, triglycerides, monoglycerides, diglycerides, phospholipids, sterols, waxes, and free fatty acids. Edible directory 304 may include a fiber tableset 316. Fiber tableset 316 may relate to a nourishment composition of an edible with respect to the quantity and/or type of fiber in the edible. As a non-limiting example, fiber tableset 316 may include soluble fiber, such as beta-glucans, raw guar gum, psyllium, inulin, and the like thereof as well as insoluble fiber, such as wheat bran, cellulose, lignin, and the like thereof. Edible directory 304 may include a mineral tableset 320. Mineral tableset 320 may relate to a nourishment composition of an edible with respect to the quantity and/or type of minerals in the edible. As a non-limiting example, mineral tableset 320 may include calcium, phosphorous, magnesium, sodium, potassium, chloride, sulfur, iron, manganese, copper, iodine, zing, cobalt, fluoride, selenium, and the like thereof. Edible directory 304 may include a protein tableset 324. Protein tableset 324 may relate to a nourishment composition of an edible with respect to the quantity and/or type of proteins in the edible. As a non-limiting example, protein tableset 324 may include amino acids combinations, wherein amino acids may include, without limitation, alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and the like thereof. Edible directory 304 may include a vitamin tableset 328. Vitamin tableset 328 may relate to a nourishment composition of an edible with respect to the quantity and/or type of vitamins in the edible. As a non-limiting example, vitamin tableset 328 may include vitamin A, vitamin $B_1$, vitamin $B_2$, vitamin $B_3$, vitamin $B_5$, vitamin $B_6$, vitamin $B_7$, vitamin $B_9$, vitamin $B_{12}$, vitamin C, vitamin D, vitamin E, vitamin K, and the like thereof.

Figure 4:
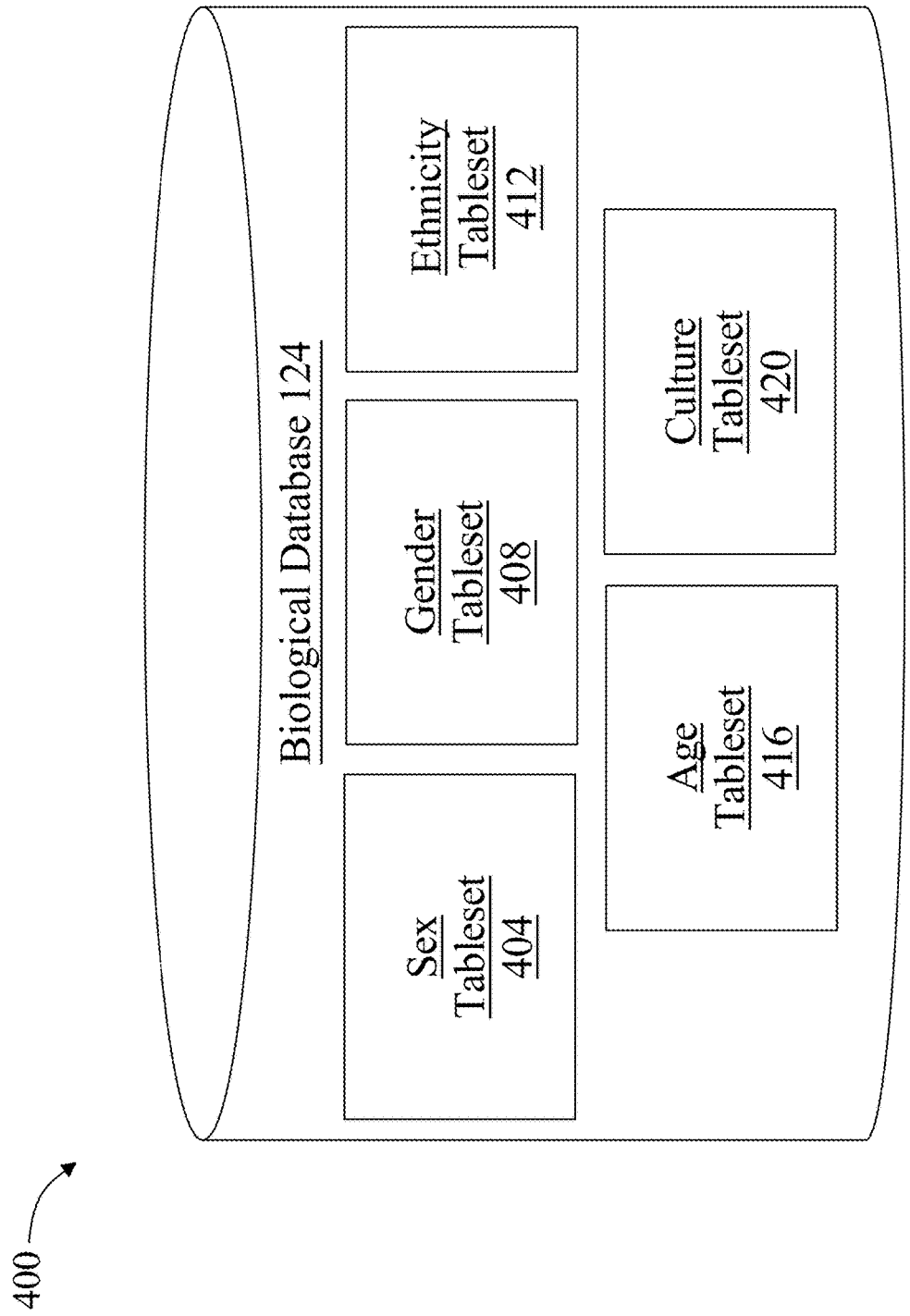
FIG. 4 is a block diagram of an exemplary embodiment of a biological database according to an embodiment of the invention.

Now referring to FIG. 4, an exemplary embodiment 400 of a biological database 124 according to an embodiment of the invention is illustrated. Biological database 124 may be implemented, without limitation, as a relational databank, a key-value retrieval databank such as a NOSQL databank, or any other format or structure for use as a databank that a person skilled in the art would recognize as suitable upon review of the entirety of this disclosure. Biological database 124 may alternatively or additionally be implemented using a distributed data storage protocol and/or data structure, such as a distributed hash table or the like. Biological database 124 may include a plurality of data entries and/or records as described above. Data entries in a databank may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a databank may store, retrieve, organize, and/or reflect data and/or records as used herein, as well as categories and/or populations of data consistently with this disclosure. Biological database 124 may include a sex tableset 404. Sex tableset 404 may include one or more sex-specific biomarkers that distinguish one or more ilk parameters relating to the sex of a subject. As a non-limiting example, sex tableset 404 may include 41249_at (LPL: lipoprotein lipase), 41755_at (COBLL1: COBL-like 1), 39878_at (PCDH9: protocadherin 9), 38211_at (ZBTB20: zinc finger and BTB domain containing 20), 39488_at (PCDH9: protocadherin 9), 36886_f at (KIR2DL3: killer cell immunoglobulin-like receptor, two domains, long cytoplasmic tail, 3), 32144_at (SORL1: sortilin-related receptor, L(DLR class) A repeats-containing), 33535_at (P2RX1: purinergic receptor P2X, ligand-gated ion channel, 1), 39967_at (LDOC1: leucine zipper, down-regulated in cancer 1), 32842_at (BCL7A: B-cell CLL/lymphoma 7A), 36899_at (SATB1: special AT-rich sequence binding protein 1 (binds to nuclear matrix/scaffold-associating DNA's)), 33745_at (PHKG2: phosphorylase kinase, gamma 2 (testis)), 38156_at (LOH11CR2A: loss of heterozygosity, 11, chromosomal region 2, gene A), 34142_at (PDE8A: phosphodiesterase 8A), 39593_at (FGL2: fibrinogen-like 2), and 217_at (KLK2: kallikrein 2, prostatic), and the like thereof. Biological database 124 may include a gender tableset 408. Gender tableset 408 may include one or more gender-specific biomarkers that distinguish one or more ilk parameters relating to the gender of a subject. As a non-limiting parameter gender tableset 408 may relate to the cortical thickness of a subject and/or the level of activation of the right superior frontal gyms. Biological database 124 may include an ethnicity tableset 412. Biological database 124 may include one or more ethnicity-specific biomarkers that distinguish one or more ilk parameters relating to the ethnicity of a subject. As a no-limiting example ethnicity tableset 412 may include NTproBNP, hsCRP, CysC, MPO, hsTnI, and the like thereof. Ethnicity tableset 416 may include an age tableset 416. Age tableset 416 may include one or more age-specific biomarkers that distinguish one or more ilk parameters relating to the age of a subject. As a non-limiting example age tableset 416 may include SBP, DBP, HDL ratio, cholesterol, triglycerides, HB1Ac, weight, height, BMI, waist circumference, hip circumference, creatine clearance, albumin, leukocyte count, IL-6, urinary cortisol, epinephrine, norepinephrine, dopamine, and the like thereof. Biological database 124 may include a culture tableset 420. Culture tableset 420 may include one or more culture-specific biomarkers that distinguish one or more ilk parameters relating to the culture of a subject. As a non-limiting example culture tableset 420 may include 3-methylindole, succinyl acetone, S-methyl-L-thiocitrulline,O-arachidonoyl glycidol, and the like thereof.

Figure 5:
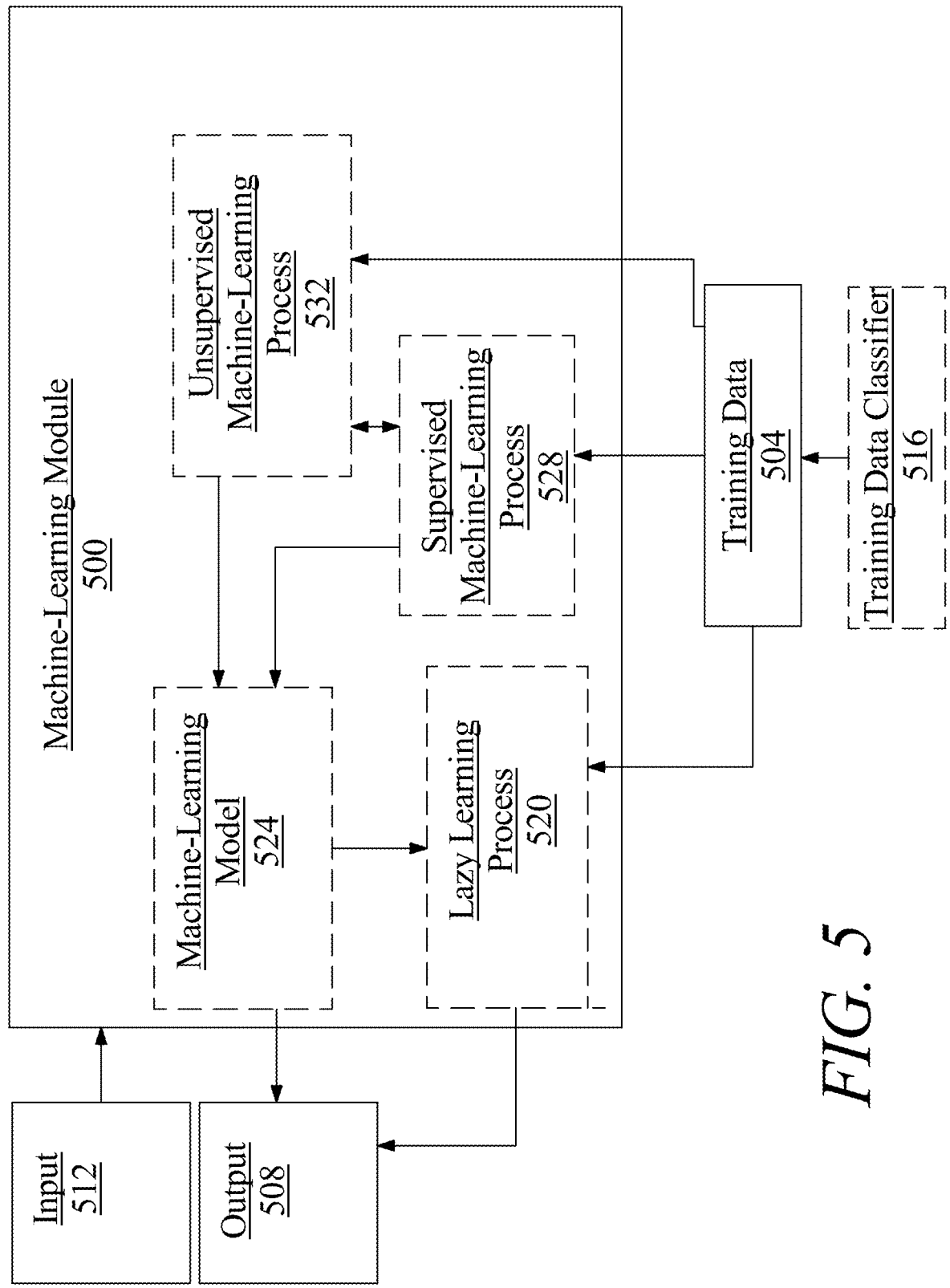
FIG. 5 is a block diagram of an exemplary embodiment of a machine-learning module.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example inputs may include ilk parameters and/or procreant markers, wherein a procreant fascicle is outputted.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 516 may classify elements of training data to sub-categories of ilk parameters including sex, gender, age, culture, and the like thereof.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements as a function of a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include ilk parameters and/or procreant markers as described above as inputs, procreant fascicles as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 6:
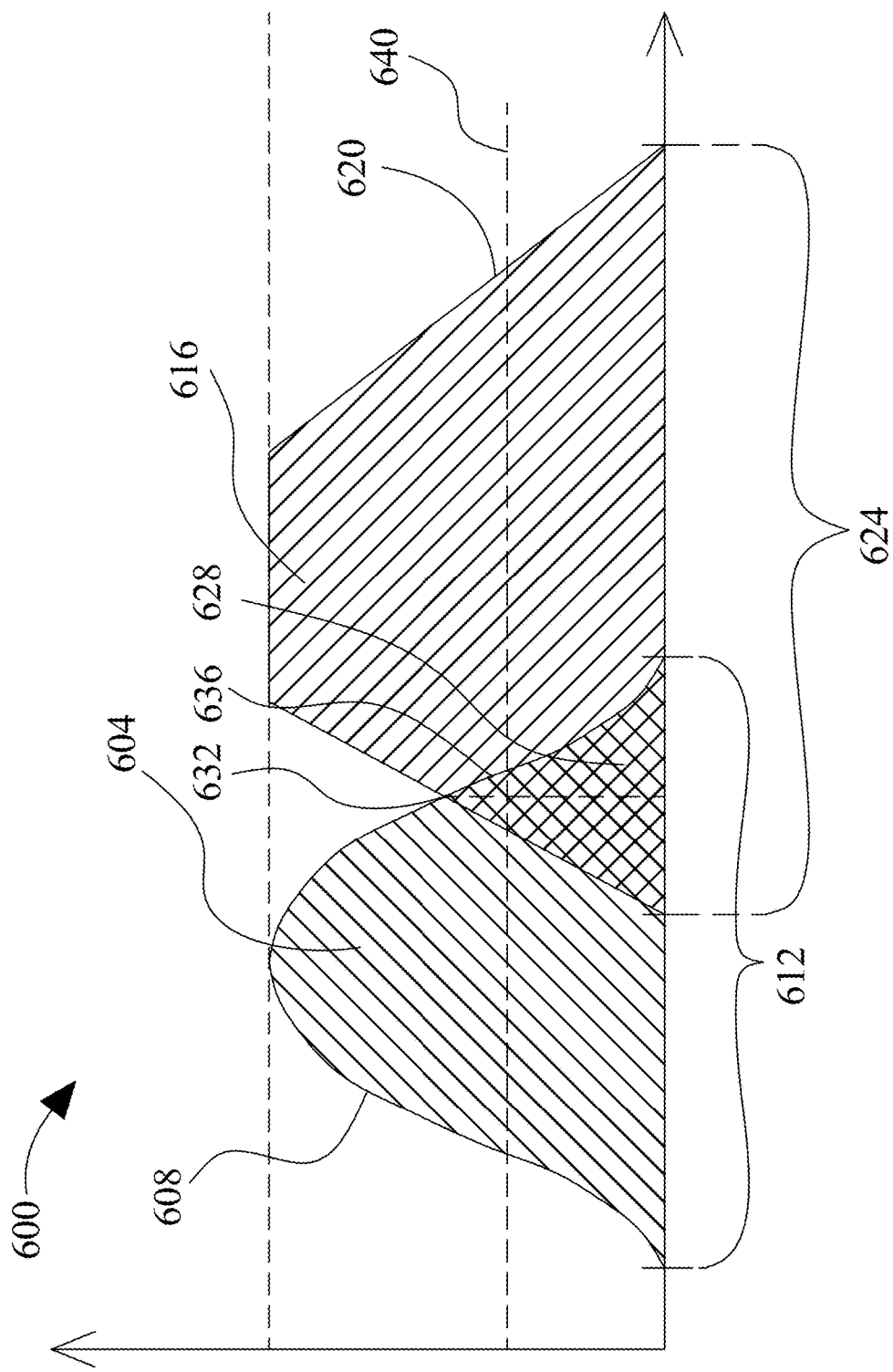
FIG. 6 is a block diagram of an exemplary embodiment of a safe range.

Referring now to FIG. 6, an exemplary embodiment of safe range 600 is illustrated. A first safe range 604 may be represented, without limitation, according to a first membership function 608 representing a probability that an input falling on a first range of values 612 is a member of the first safe range 604, where the first membership function 208 has values on a range of probabilities such as without limitation the interval [0,1], and an area beneath the first membership function 608 may represent a set of values within first safe range 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c) = \begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d) = \max\left(\min\left(\frac{x-a}{b-a}, 1, \frac{d-x}{d-c}\right), 0\right)$$

a sigmoidal function may be defined as:

$$y(x, a, c) = \frac{1}{1 - e^{-a(x-c)}}$$

a Gaussian membership function may be defined as:

$$y(x, c, \sigma) = e^{\frac{1}{2}\left(\frac{x-c}{\sigma}\right)^2}$$

and a bell membership function may be defined as:

$$y(x, a, b, c,) = \left[1 + \left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 6, first safe range 204 may represent any value or combination of values as described above, including procreant enumeration 136, any resource datum, any niche datum, and/or any combination of the above. A second safe range 216, which may represent any value which may be represented by first safe range 204, may be defined by a second membership function 220 on a second range 224; second range 224 may be identical and/or overlap with first range 212 and/or may be combined with first range via Cartesian product or the like to generate a mapping permitting evaluation overlap of first fuzzy set 204 and second safe range 216. Where first safe range 204 and second safe range 216 have a region 228 that overlaps, first membership function 208 and second membership function 220 may intersect at a point 232 representing a probability, as defined on probability interval, of a match between first safe range 204 and second safe range 216. Alternatively or additionally, a single value of first and/or second fuzzy set may be located at a locus 236 on first range 212 and/or second range 224, where a probability of membership may be taken by evaluation of first membership function 208 and/or second membership function 220 at that range point. A probability at 228 and/or 232 may be compared to a threshold 240 to determine whether a positive match is indicated. Threshold 240 may, in a non-limiting example, represent a degree of match between first safe range 204 and second safe range 216, and/or single values therein with each other or with either set, which is sufficient for purposes of the matching process; for instance, threshold may indicate a sufficient degree of overlap between procreant enumeration 136 and output procreant appraisal 144 for combination to occur as described above. Each threshold may be established by one or more procreant recommendations 152. Alternatively or additionally, each threshold may be tuned by a machine-learning and/or statistical process, for instance and without limitation as described in further detail below.

Figure 7:
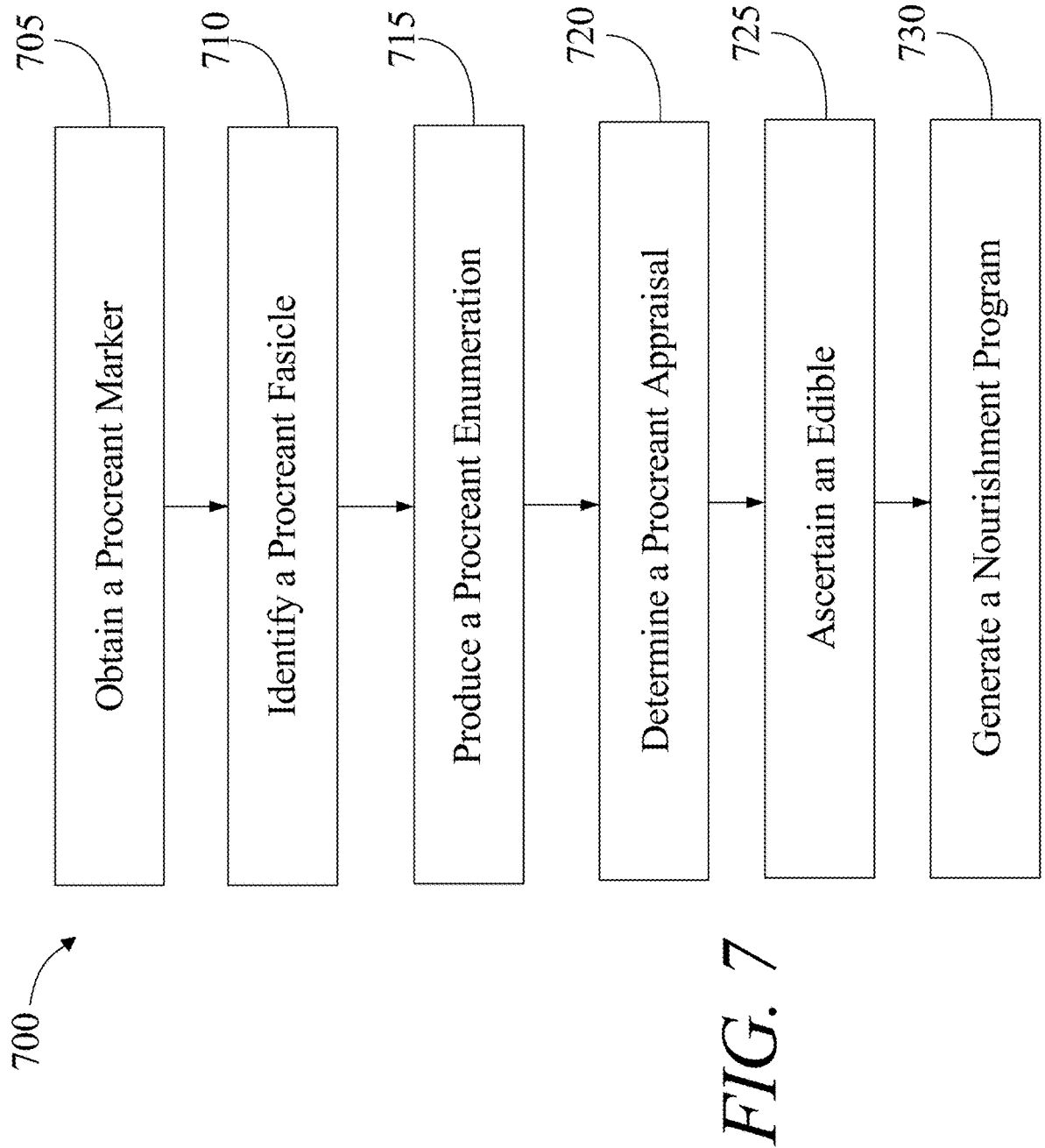
FIG. 7 is a process flow diagram illustrating an exemplary embodiment of a method of generating a procreant nourishment program.

Now referring to FIG. 7 an exemplary embodiment of a method 700 for generating a procreant nourishment program is illustrated. At step 705, a computing device 104 obtains at least a procreant marker 108 as a function of a procreant system 112. Computing device 104 includes any of the computing device 104 as described above, in reference to FIGS. 1-6. Procreant marker 108 includes any of the procreant marker 108 as described above, in reference to FIGS. 1-6. Procreant system 112 includes any of the procreant system 112 as described above, in reference to FIGS. 1-6.

Still referring to FIG. 7, at step 710, computing device 104 identifies a procreant fascicle 116 as a function of procreant marker 108. Procreant fascicle 116 includes any of the procreant fascicle 116 as described above, in reference to FIGS. 1-6. Computing device 104 receives an ilk parameter 120 as a function of a biological database 124. Ilk parameter 120 includes any of the ilk parameter 120 as described above, in reference to FIGS. 1-6. Biological database 124 includes any of the biological database 124 as described above, in reference to FIGS. 1-6. Computing device 104 retrieves at least a procreant functional goal 128. Functional goal 128 includes any of the functional goal 128 as described above, in reference to FIGS. 1-6. Computing device identifies procreant fascicle 116 as a function of ilk parameter 120, procreant functional goal 128, and procreant marker 108 using a procreant machine-learning model 132. Procreant machine-learning model 132 includes any of the procreant machine-learning model 132 as described above, in reference to FIGS. 1-6.

Still referring to FIG. 7, at step 715, computing device produces a procreant enumeration 136 using an enumeration machine-learning model 140. Procreant enumeration 136 includes any of the procreant enumeration 136 as described above, in reference to FIGS. 1-6. Enumeration machine-learning model 140 includes any of the enumeration machine-learning model as described above, in reference to FIGS. 1-6.

Still referring to FIG. 7, at step 720, computing device 104 determines a procreant appraisal 144 as a function of procreant enumeration 136. Procreant appraisal 144 includes any of the procreant appraisal 144 as described above, in reference to FIGS. 1-6. Computing device determines procreant appraisal 144 by receiving a safe range 148 as a function of a procreant recommendation 152. Safe range 148 includes any of the safe range 148 as described above, in reference to FIGS. 1-6. Procreant recommendation 152 includes any of the procreant recommendation 152 as described above, in reference to FIGS. 1-6.

Still referring to FIG. 7, at step 725, computing device 104 ascertains at least an edible 156 as a function of procreant appraisal 136. Edible 156 includes any of the edible 156 as described above, in reference to FIGS. 1-6.

Still referring to FIG. 7, at step 730, computing device 104, generates a nourishment program 160 of a plurality of nourishment programs as a function of edible 156. Nourishment program 160 includes any of the nourishment program 160 as described above, in reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
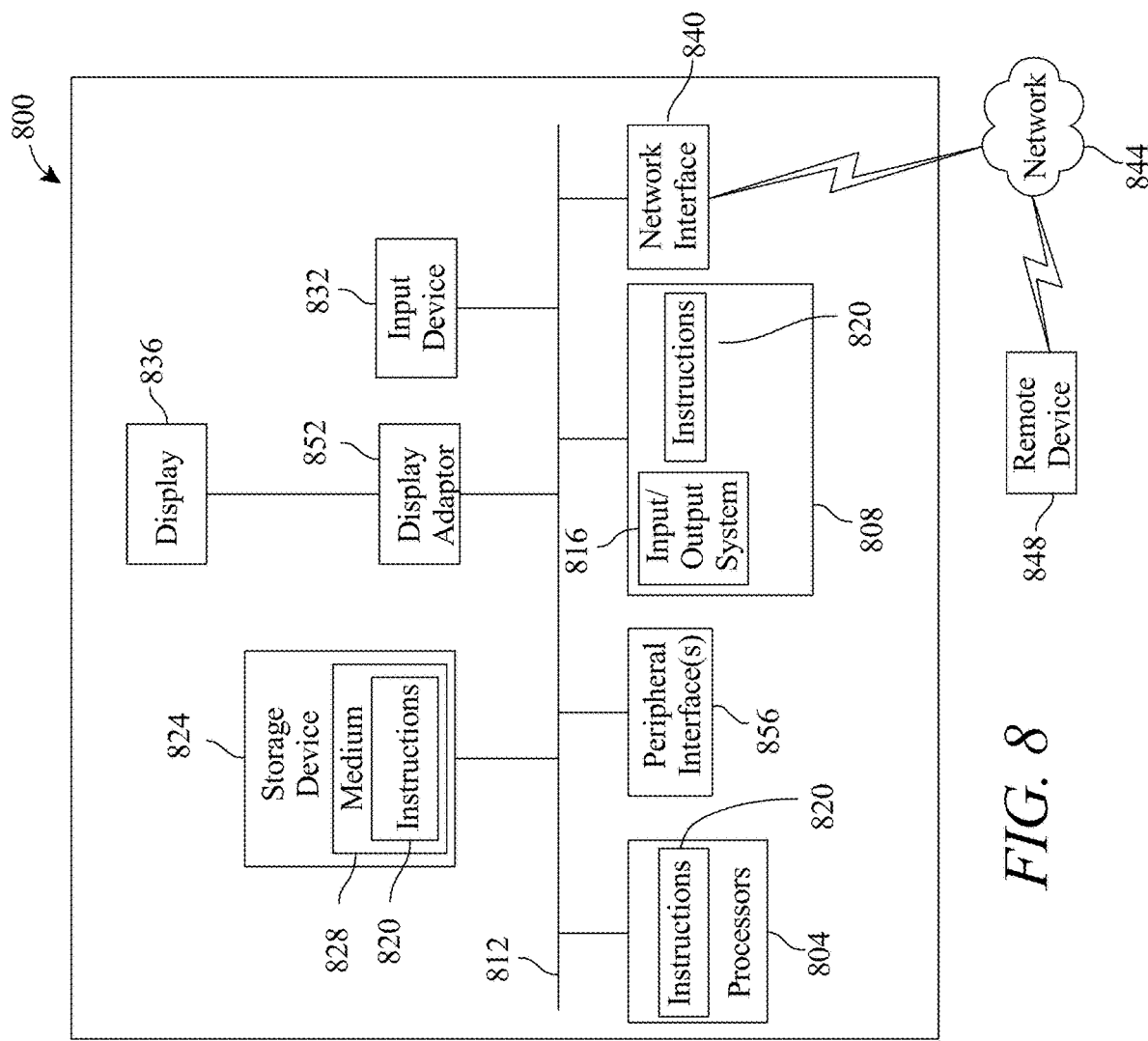
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for generating a procreant nourishment program, the system comprising:
a computing device, the computing device configured to:
obtain at least a procreant marker as a function of a procreant system;
identify a procreant fascicle as a function of the procreant marker, wherein identifying comprises:
receiving an ilk parameter as a function of a biological database;
retrieving at least a procreant functional goal; and
identifying the procreant fascicle as a function of the ilk parameter, the at least a procreant functional goal, and the at least a procreant marker using a procreant machine-learning model;
produce a procreant enumeration as a function of the procreant fascicle using an enumeration machine-learning model;
determine a procreant appraisal as a function of the procreant enumeration, wherein determining comprises:
receiving a safe range as a function of a procreant recommendation; and
determining the procreant appraisal as a function of the procreant enumeration and safe range;
ascertain an edible as a function of the procreant appraisal;
generate a nourishment program of a plurality of nourishment programs as a function of the edible.

2. The system of claim 1, wherein obtaining the at least a procreant marker includes receiving a procreant signal from a sensor and obtaining the at least a procreant marker as a function of the procreant signal.

3. The system of claim 2, wherein the sensor includes a medical examination device.

4. The system of claim 1, wherein identifying the procreant fascicle further comprises:
receiving a synergistic parameter as a function of the at least a procreant marker;
generating a procreant cluster as a function of the synergistic parameter; and
identifying the procreant fascicle as a function of the procreant cluster.

5. The system of claim 1, wherein producing the procreant enumeration includes identifying a procreant disorder and producing the procreant enumeration as a function of the procreant disorder.

6. The system of claim 5, wherein identifying the procreant disorder further comprises:
obtaining a disorder training set; and
determining the procreant disorder using the procreant fascicle and a disorder machine-learning model, wherein the procreant machine-learning model is trained as a function of the disorder training set.

7. The system of claim 1, wherein determining the procreant appraisal further comprises:
generating a degree of variance as a function of the procreant enumeration and the safe range; and
determining the procreant appraisal as a function of the degree of variance and a procreant threshold.

8. The system of claim 1, wherein ascertaining the edible further comprises:
obtaining a nourishment composition from an edible directory; and
ascertaining an edible using the nourishment composition, the procreant appraisal, and an edible machine-learning model.

9. The system of claim 1, wherein ascertaining the edible further comprises:
determining a likelihood parameter, wherein the likelihood parameter relates a user taste profile to an edible profile; and
ascertaining the edible as a function of the likelihood parameter.

10. The system of claim 1, wherein generating the nourishment program further comprises:
obtaining a procreant outcome; and
generating the nourishment program as a function of the edible and the procreant outcome using a nourishment machine-learning model.

11. A method for generating a procreant nourishment program, the method comprising:
obtaining, by a computing device, at least a procreant marker as a function of a procreant system;
identifying, by the computing device, a procreant fascicle as a function of the procreant marker, wherein identifying comprises:
receiving an ilk parameter as a function of a biological database;
retrieving at least a procreant functional goal; and
identifying the procreant fascicle as a function of the ilk parameter, the at least a procreant functional goal, and the at least a procreant marker using a procreant machine-learning model;
producing, by the computing device, a procreant enumeration as a function of the procreant fascicle using an enumeration machine-learning model;
determining, by the computing device, a procreant appraisal as a function of the procreant enumeration, wherein determining comprises:
receiving a safe range as a function of a procreant recommendation; and
determining the procreant appraisal as a function of the procreant enumeration and safe range;
ascertaining, by the computing device, an edible as a function of the procreant appraisal;
generating, by the computing device, a nourishment program of a plurality of nourishment programs as a function of the edible.

12. The method of claim 11, wherein obtaining the at least a procreant marker includes receiving a procreant signal from a sensor and obtaining the at least a procreant marker as a function of the procreant signal.

13. The method of claim 12, wherein the sensor includes a medical examination device.

14. The method of claim 11, wherein identifying the procreant fascicle further comprises:
receiving a synergistic parameter as a function of the procreant marker;
generating a procreant cluster as a function of the synergistic parameter; and
identifying the procreant fascicle as a function of the procreant cluster.

15. The method of claim 11, wherein producing the procreant enumeration includes identifying a procreant disorder and producing the procreant enumeration as a function of the procreant disorder.

16. The method of claim 15, wherein identifying the procreant disorder further comprises:
obtaining a disorder training set; and
determining the procreant disorder using the procreant fascicle and a disorder machine-learning model, wherein the procreant machine-learning model is trained as a function of the disorder training set.

17. The method of claim 11, wherein determining the procreant appraisal further comprises:
generating a degree of variance as a function of the procreant enumeration and the safe range; and
determining the procreant appraisal as a function of the degree of variance and a procreant threshold.

18. The method of claim 11, wherein ascertaining the edible further comprises:
obtaining a nourishment composition from an edible directory; and
ascertaining an edible using the nourishment composition, the procreant appraisal, and an edible machine-learning model.

19. The method of claim 11, wherein ascertaining the edible further comprises:
determining a likelihood parameter, wherein the likelihood parameter relates a user taste profile to an edible profile; and
ascertaining the edible as a function of the likelihood parameter.

20. The method of claim 11, wherein generating the nourishment program further comprises:
obtaining a procreant outcome; and
generating the nourishment program as a function of the edible and the procreant outcome using a nourishment machine-learning model.

* * * * *